Figure 1:
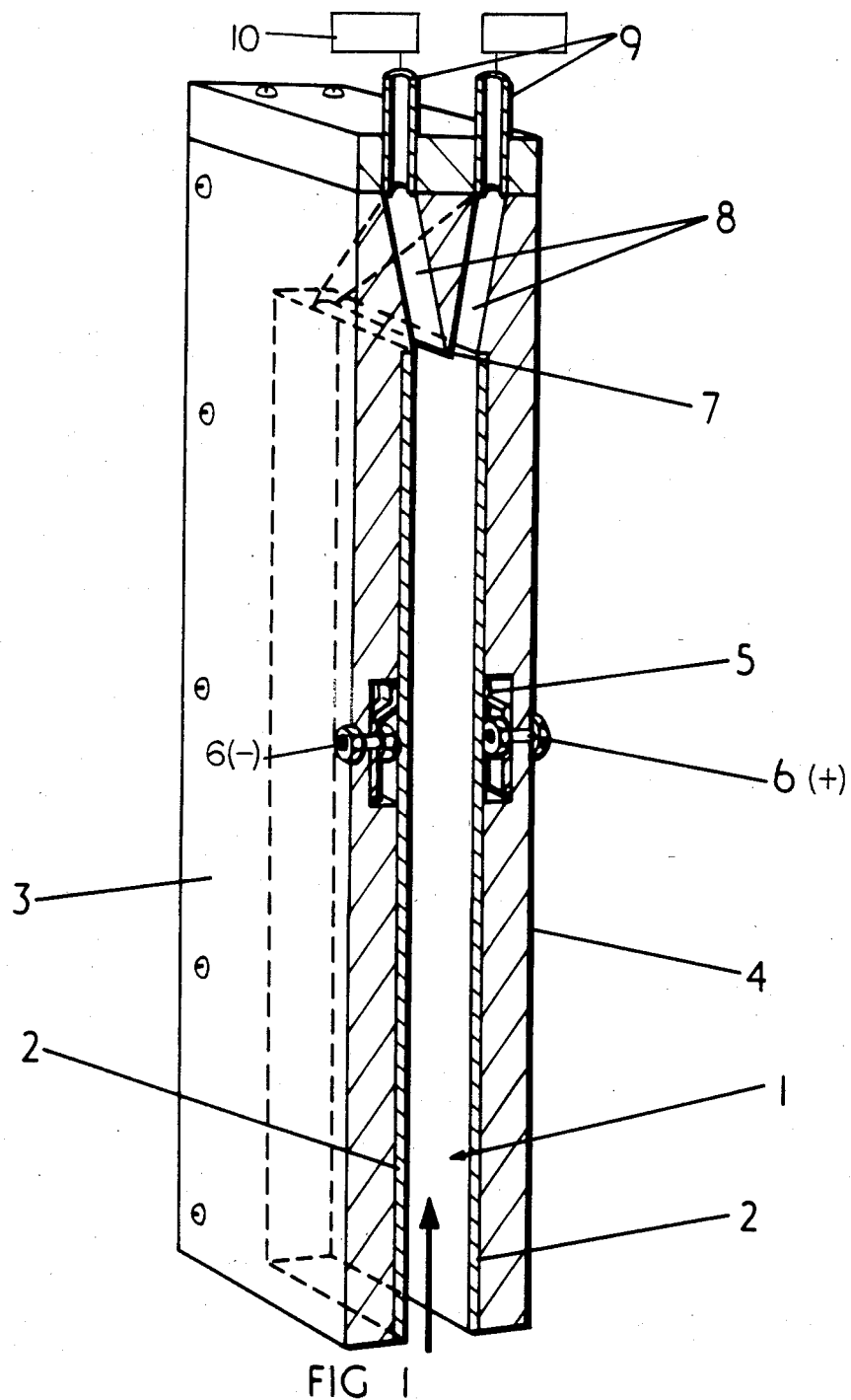

United States Patent [19]

Johnston

[11] Patent Number: 4,555,933
[45] Date of Patent: Dec. 3, 1985

[54] DUST ASSESSMENT APPARATUS AND METHOD

[75] Inventor: Arthur M. Johnston, Roslin, Scotland

[73] Assignee: Coal Industry (Patents) Limited, London, England

[21] Appl. No.: 577,955

[22] Filed: Feb. 8, 1984

[30] Foreign Application Priority Data

Feb. 18, 1983 [GB] United Kingdom ............... 8304549

[51] Int. Cl.⁴ .................. G01N 15/02; G01N 27/60
[52] U.S. Cl. .................................. 73/28; 209/129; 209/130
[58] Field of Search .......... 55/270, 2, 136, 154; 73/28, 863.21, 863.22, 863.23; 209/128, 130, 129

[56] References Cited

U.S. PATENT DOCUMENTS

| 959,646 | 5/1910 | Swart | 209/127 A |
| 3,295,359 | 1/1967 | Peck | 55/270 |
| 3,628,139 | 12/1971 | Huber | 73/28 |
| 3,853,750 | 12/1974 | Volsy | 73/28 |
| 3,868,222 | 2/1975 | Barringer | 73/863.23 |
| 4,140,005 | 2/1979 | Kittelson | 73/28 |

FOREIGN PATENT DOCUMENTS

2083619 3/1982 United Kingdom .

Primary Examiner—Bernard Nozick
Attorney, Agent, or Firm—James C. Wray

[57] ABSTRACT

A gas containing dispersed particles with differing electrostatic charges is drawn through a gas channel between opposite charged plates before being split into equal gas flows by a flow divider. The equal gas flows leave the apparatus through exits which can be connected to a particle counter.

7 Claims, 1 Drawing Figure

DUST ASSESSMENT APPARATUS AND METHOD

This invention concerns apparatus and a method for assessing airborne dust, more particularly for assessing the distribution of the magnitude and polarity of the electrostatic charge on airborne dust.

Airborne dust has been associated with a number of health problems, and instruments for the collection of dust have been manufactured and used to assess the risks of exposure of persons in dusty environments. Studies have been made of the size distribution of airborne dust, particularly since some size ranges are much more liable to be deposited in the body then others. It is now suggested that dust particles carrying charges, for example caused by the normal mechanical action giving rise to the creation of the airborne dust, are deposited to a much greater extent in lungs than similar dust which is electrically neutral. A study of rats exposed to asbestos dust shows that those exposed to charged dusts receive a lung burden up to twice that of rats exposed to neutralised fibres. It appears that charge effects could be of considerable importance with regard to dust-related health effects, in particular for aerodynamically fine dusts where deposition by inertial and gravitational mechanisms alone is not very efficient.

The present invention provides apparatus for the assessment of the magnitude of charge and polarity of electrostatically charged gas-borne dust particles, comprising a gas flow channel having opposite walls of electrically conductive material and means for imparting different states of electrical charge to the said opposite walls, and a flow divider to divide gas flow in the channel having passed the opposite walls into a plurality of separate gas flows carrying particles distributed by the effect of the different charges on the walls. Conveniently the flow divider splits the gas flow into two equal gas flows, each associated with a gas exit.

The invention also provides a method of assessing the magnitude of charge and polarity of electrostatically charged dust particles suspended in a gas, comprising the application of different states of charge to the opposite walls of the apparatus of the invention, the passage of the gas through the apparatus and the assessment of the dust distribution in the separate gas flows after division by the flow divider.

Each separate gas flow exit is preferably connectible to a particle counter, such as an automatic optical particle counter. At least one exit is connectible directly or indirectly to pump means for inducing gas flow through the apparatus, and gas flow should be limited to give laminar flow.

The apparatus gas flow channel is preferably rectangular in section, with the chargeable opposite walls being metal plates forming at least part of the major faces of the rectangular channel. A central knife-edge flow divider is preferably mounted at the exit end of the channel, to split the gas flow equally. The metal plates are connectible to means for imparting different states of electrical charge; normally one plate is earthed and the other plate may be at a positive or negative potential of up to 10,000 V or more. Preferably, the apparatus is set up to avoid gravitational effects on the particles in the gas stream and in the preferred apparatus, the plane extending through the flow divider is vertical.

In using the invention, charged airborne particles are drawn through the channel, and the particles will be drawn to one or other of the walls, depending upon the particle size and magnitude of the charge carried. Some particles will be collected on the charged walls, others will pass completely through the channel but will be distributed in one or other of the separate gas flows. It is relatively straightforward to measure Penetration (P), which is the ratio of the number of particles passing through the instrument to the number of particles entering, and this can be done for a range of applied voltages. The state of charge of the dust can be determined from the relationship between P and V, and also it is possible to derive, using the apparatus and method of the invention, values for particle mobility and the number of particles of a given diameter having that mobility.

One embodiment of the invention will now be described by way example, with reference to the accompanying drawing, which is a perspective view partially in section of an apparatus according to the invention.

A rectangular gas flow channel, 1, is defined by major walls, 2, and minor walls, 3 (one only shown in outline). The major walls are formed entirely of stainless steel plates, and the side walls, and the rest of the body, 5, of the apparatus are formed of high resistivity laminated resin-impregnated board. Each major wall is in contact with spring clips, 5, attached to terminals, 6, passing through the body of the apparatus. At the exit end of the channel a central knife-edge flow divider, 7, extends across the entire width of the channel and separate gas flow channels, 8, lead into first and second gas exits, 9. The direction of gas flow is indicated by an arrow.

The apparatus is set up with the major plate planes and the plane extending through the flow divider, vertical, to avoid gravitational effects on the particles. Two different operating modes have been used, these have been selected according to the nature of the dust to be assessed and the information required. Both exits 9 may be connected to an optical particle counter 10 (Royco Instruments Model 267) and to a rotary pump. Alternatively, one exit is connected to a particle counter and the other is connected via an in-line filter and a rotometer flow measurer to the pump, the flow rates through each exit being equalised. In the latter case, the particle counter may be attached to either of the exits, thus increasing the amount of information available.

In the embodiment which has been tested and is in accordance with FIG. 1, flow rates of 2 to 3 liters per minute over the particle counter have been found to be suitable in most environments, to avoid overloading the counter with particles, to give a reasonable time of passage through the apparatus and to ensure laminar flow at lest to the flow divider. Such flow rates may of course be varied according to the dimensions of the apparatus, the design of particle counter and for other reasons.

The desired particle size range may be set on the counter, and the applied voltage is slowly swept to obtain a penetration curve, then the polarity is reversed and the sweep repeated. The maximum voltage available should be at least that necessary to reduce the penetration to 5% of its zero volt value, unless the curve of penetration against voltage becomes flat at a higher value. If the sufficiently high voltage range is not available, a penetration curve can be obtained by connecting both exits to the particle counter.

It is envisaged that a micro-computer could control the voltage sweeps, the data gathering fom the particle counter and the analysis of the data. If the dust level in any atmosphere is very variable, the output from the ambient dust concentration measurement instrument could be correlated with the information available through the instrument of the invention.

I claim:

1. Apparatus for the assessment of the magnitude of charge and polarity of electrostatically charged gas-borne dust particles, comprising a gas flow conduit having opposite walls of electrically conductive material means for imparting different states of electrical charge to the said opposite walls, and a flow divider located in the conduit to divide gas flow in the conduit having passed the opposite walls into a plurality of separate gas flows carrying particles distributed by the effect of the different charges on the walls, separate conduits to receive each separate gas flow and a gas flow exit connected to each separate conduit, and means connected to each gas flow exit, for assessing the magnitude of charge and polarity of electrically charged gas-borne dust particles.

2. Apparatus as claimed in claim 1, wherein the gas flow conduit is rectangular in section, and the chargeable opposite walls are metal plates forming at least part of the major faces of the conduit and being separated by opposite nonconducted walls.

3. Apparatus as claimed in claim 1, wherein the flow divider is a central knife-edge flow divider, which acts to split the gas flow equally.

4. The apparatus of claim 1, wherein the means for assessing comprises a particle counter connected to each separate gas flow exit.

5. A method of assessing the magnitude of charge and polarity of electrostatically charged dust particles suspended in a gas, comprising the application of different states of electrical charge to opposite walls of electrically conductive material and located in a gas flow conduit, flowing the gas through the conduit dividing the gas flow downstream of the charged opposite walls and assessing the dust distribution in each fraction of the divided gas flow.

6. A method as claimed in claim 5, wherein the assessment of dust distribution is carried out by passing the separate gas flows through a particle counter.

7. A method as claimed in claim 6, wherein different voltages are applied to the opposite walls, the number of particles entering the conduit is counted, the total number of particles leaving the conduit is counted, and a value for penetration being the ratio of the total number of particles in the separate gas flows to the number of particles entering the conduit, is calculated.

* * * * *